United States Patent
Momoi

(10) Patent No.: US 7,867,513 B2
(45) Date of Patent: Jan. 11, 2011

(54) SOFT CAPSULE

(75) Inventor: Kazuhisa Momoi, Gifu (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 1184 days.

(21) Appl. No.: 11/504,398

(22) Filed: Aug. 15, 2006

(65) Prior Publication Data

US 2007/0042035 A1 Feb. 22, 2007

Related U.S. Application Data

(63) Continuation of application No. PCT/JP2005/002313, filed on Feb. 16, 2005.

(30) Foreign Application Priority Data

Feb. 17, 2004 (JP) .............................. 2004-040116

(51) Int. Cl.
*A61K 9/48* (2006.01)
(52) U.S. Cl. ..................................................... 424/451
(58) Field of Classification Search .................. 424/451
See application file for complete search history.

(56) References Cited

U.S. PATENT DOCUMENTS

| 5,955,327 | A | 9/1999 | Hirai et al. | |
| 2004/0182283 | A1* | 9/2004 | Steffenino et al. | 106/162.8 |

FOREIGN PATENT DOCUMENTS

| CN | 1197115 A | 10/1998 |
| CN | 200580005247.1 | 6/2009 |
| GB | 1 324 242 | 7/1973 |
| JP | 49-11047 | 3/1974 |
| JP | 56-156212 | 12/1981 |
| JP | 64-042419 | 2/1989 |
| JP | 64-079110 | 3/1989 |
| JP | 2-022221 | 1/1990 |
| JP | 3-098638 | 4/1991 |
| JP | 03139246 A * | 6/1991 |
| JP | 4-288011 | 10/1992 |
| JP | 5-004914 | 1/1993 |
| JP | 7-173065 | 7/1995 |
| JP | 8-034727 | 2/1996 |
| JP | 8-169817 | 7/1996 |
| JP | 10-310519 | 11/1998 |
| JP | 11-019503 | 1/1999 |
| JP | 2000-44465 | 2/2000 |
| JP | 2000-336028 | 12/2000 |
| JP | 2001-161306 | 6/2001 |
| JP | 2002-154949 | 5/2002 |
| JP | 2002-532389 | 10/2002 |
| JP | 2003-192578 | 7/2003 |
| WO | 00/33817 | 6/2000 |

* cited by examiner

*Primary Examiner*—Michael G Hartley
*Assistant Examiner*—James W Rogers
(74) *Attorney, Agent, or Firm*—Carmody & Torrance LLP

(57) ABSTRACT

It is an object of the present invention to provide a capsule anti-sticking agent which can provide excellent anti-sticking effect on a soft capsule without impairing various properties such as water activity, disintegration property and safety, a coated soft capsule of high quality which is coated with the capsule anti-sticking agent and excels in anti-sticking effect, and an efficient method for manufacturing the coated soft capsule.

The present invention includes a capsule anti-sticking agent containing an enzymatically decomposed lecithin, a coated soft capsule wherein a surface is coated with the capsule anti-sticking agent, and a method for manufacturing the coated soft capsule in which a surface of a soft capsule is coated with the capsule anti-sticking agent.

2 Claims, No Drawings

SOFT CAPSULE

CROSS-REFERENCE TO RELATED APPLICATIONS

This is a continuation of Application No. PCT/JP2005/002313 filed on Feb. 16, 2005

BACKGROUND OF THE INVENTION

1. Field of the Invention

The present invention is to provide a capsule anti-sticking agent which can provide excellent anti-sticking effect on soft capsules without impairing various properties such as water activity, disintegration property and safety, a coated soft capsule of high quality which is coated with the capsule anti-sticking agent and excels in anti-sticking effect and an efficient method for manufacturing the coated soft capsule.

2. Description of the Related Art

Soft capsules have been used in a wide range of fields such as medicaments, cosmetics, foods and health foods because they are formed by membrane materials containing gelatin as main ingredient and can conveniently encapsulate oily liquids, granule, powder, tablets and the like.

However, conventional soft capsules get moistened and softened because of their hygroscopic property when stored in high temperature and high humidity environment like in summer or rainy season (at a temperature of 40° C. and a relative humidity of 75% or more, for example). As a result, adhesive property of surface of the soft capsules may be increased and sliding property of the soft capsules may be decreased, making packing and filling operations difficult, or the soft capsules may stick to each other or to the inner surface of the storage containers, and taking out of required amount of soft capsules may become difficult or the capsule membrane may be destroyed at the time of ingestion.

Therefore, various methods have been proposed in order to prevent sticking between soft capsules or between the soft capsules and the inner surface of the storage containers. For example, a method for coating surfaces of the soft capsules with anti-sticking agents (coating agents), a method for mixing anti-sticking ingredients in the membrane material of the soft capsules, and the like are known.

In the method for coating surfaces of the soft capsules with anti-sticking agents (coating agents), hydroxypropylmethylcellulose, and shellac, ethylcellulose and alkylene glycol as necessary (Japanese Patent Application Publication (JP-B) No. 49-11047), carnauba wax (Japanese Patent Application Laid-Open (JP-A) No. 56-156212), hardened oil such as castor oil, rapeseed oil, cotton-seed oil and soybean oil (JP-A No. 64-42419), hardened vegetable oil or sucrose esters of fatty acid (JP-A No. 64-79110), glyceryl fatty acid diacetate (JP-A No. 4-288011) and mixtures of film-forming materials such as cellulose derivatives and inorganic materials or organic acid metal salt (JP-A No. 8-34727) have been proposed as the anti-sticking agents, for example. However, when the soft capsules coated with these anti-sticking agents are stored in high temperature and high humidity conditions, the surface adhesive property is increased with time and anti-sticking effect becomes insufficient.

On the other hand, in the method for mixing anti-sticking ingredients in the membrane material of the soft capsules, the anti-sticking ingredients and the capsule contents may interact with each other, resulting in lack of versatility. Moreover, it is necessary to mix the anti-sticking ingredients with the membrane materials of the soft capsules in large amount in order to increase the anti-sticking effect and as a result, problems such as extended time for disintegration, defective appearance, formability degradation of the soft capsules, and the like during manufacturing arise (JP-A Nos. 2-22221, 3-98638, 5-4914, 8-169817, 10-310519 and 2000-44465).

For example, lecithin is proposed as the anti-sticking ingredient (JP-A No. 2000-336028), however, the anti-sticking effect provided by mixing in the lecithin is not satisfactory.

Meanwhile, lecithin which is mixed in the membrane ingredients of capsules for the purpose other than anti-sticking have been proposed. For example, an enzyme-digested lecithin as a carrier for bioactive compound (JP-A No. 2002-532389), a lecithin as an emulsifier (JP-A No. 2001-161306), a soybean lecithin as a plasticizer (JP-A No. 11-19503), an enzymatically decomposed lecithin as a flavoring ingredient (JP-A No. 2002-154949) have been proposed. However, the fact that the lecithin and the enzymatically decomposed lecithin that are mixed excel in anti-sticking effect of the soft capsules is not disclosed in these proposals.

Therefore, development of anti-sticking agent, which can provide excellent anti-sticking effect on the soft capsules without impairing various properties such as water activity, disintegration property and safety even when the soft capsules are stored in high temperature and high humidity environment, is desired.

SUMMARY OF THE INVENTION

The present invention is intended to solve above-mentioned problems and to achieve the following objects. It is an object of the present invention to provide a capsule anti-sticking agent which can provide excellent anti-sticking effect to soft capsules without impairing various properties such as water activity, disintegration property and safety, a coated soft capsule of high quality which is coated with the capsule anti-sticking agent and excels in anti-sticking effect, and an efficient method for manufacturing the coated soft capsule.

As a result of dedicated investigation conducted on the above problems, the present inventors have obtained the following knowledge. It has been found that a soft capsule with its surface being coated with the capsule anti-sticking agent containing an enzymatically decomposed lecithin excels in anti-sticking effect and is of high quality without impairment of various properties such as water activity, disintegration property and safety compared to the conventional soft capsules without the capsule anti-sticking agent on the surfaces. The coated soft capsule prevents sticking between capsules and to the storage container even when stored in high temperature and high humidity environment (at a temperature of 40° C. and a relative humidity of 75% or more, for example).

The present invention is based on the knowledge of the present inventors and the measures to solve above-mentioned problems are as follows.

<1> A capsule anti-sticking agent containing an enzymatically decomposed lecithin.

<2> The capsule anti-sticking agent as stated in above <1>, wherein the enzymatically decomposed lecithin is of any one of vegetable origin and animal origin.

<3> The capsule anti-sticking agent as stated in above <1>, wherein the enzymatically decomposed lecithin is of any one of soy bean origin and egg yolk origin.

<4> A coated soft capsule containing a capsule anti-sticking agent, wherein a surface of the coated soft capsule is coated with the capsule anti-sticking agent, and the capsule anti-sticking agent contains an enzymatically decomposed lecithin.

<5> The coated soft capsule as stated in above <4>, wherein the surface of the coated soft capsule is provided with anti-sticking effect.

<6> A method for manufacturing a coated soft capsule containing applying a capsule anti-sticking agent on a surface of a soft capsule, wherein the capsule anti-sticking agent contains an enzymatically decomposed lecithin.

DESCRIPTION OF THE PREFERRED EMBODIMENTS (Capsule Anti-Sticking Agent)

The capsule anti-sticking agent of the present invention contains an enzymatically decomposed lecithin and further contains other ingredients as necessary.

-Enzymatically Decomposed Lecithin-

The enzymatically decomposed lecithin is a lecithin decomposed with enzyme and purified as necessary. Examples include a decomposition product obtained by decomposing the lecithin, which has been pH adjusted with water or alkaline solution, with enzymes such as phospholipase and the decomposition product extracted with ethanol, isopropyl alcohol or acetone.

The main ingredient of the enzymatically decomposed lecithin is at least any one of lysolecithin and phosphatidyl acid.

An enzyme-processed lecithin containing phosphatidyl glycerol as a main ingredient is also usable as the enzymatically decomposed lecithin.

The lecithin used for manufacturing the enzymatically decomposed lecithin is not particularly limited and may be selected accordingly as long as it is a phospholipid containing phosphatidyl choline, phosphatidyl ethanolamine, phosphatidyl inositol, and the like. For example, it is preferably a lecithin obtained by being isolated from fat derived from any one of vegetable material and animal material.

Examples of vegetable material include soybean, sesame seed, corn and grain, and examples of animal material include egg yolk, small fish and liver. Among these, soybean and egg yolk are preferable.

The enzymatically decomposed lecithin is not particularly limited and may be selected accordingly as long as it contains enzymatic decomposition product of the lecithin (lysolecithin and phosphatidyl acid, for example). For example, the enzymatically decomposed lecithin is preferably satisfying the aspect, results of confirmation tests and purity tests and water content defined in "The Existing Food Additives Self-Standard, Vol. 3" by Japan Food Additives Association.

Examples of the commercially available product of the enzymatically decomposed lecithin include SLP-Paste Lyso and SLP-White Lyso by Tsuji Oil Mill Co., Ltd.; Elmizer A and Elmizer AC by Kyowa Hakko Kogyo Co., Ltd.; Benecoat BMI-40 by Kao Corp.; Sunlecithin A by Taiyo Kagaku Co., Ltd.; Basis LG-10K and Basis LP-20E by The Nisshin Oillio Group, Ltd.; and Egg Yolk Lecithin LPL-20 and Egg Yolk Lysolecithin LPC-1 by Kewpie Co., Ltd.

The content of the enzymatically decomposed lecithin relative to the whole amount of the capsule anti-sticking agent of the present invention is not particularly limited and may be adjusted accordingly. For example, the content of the enzymatically decomposed lecithin is preferably 0.0001% by mass to 2.0% by mass, more preferably 0.0005% by mass to 1.0% by mass and most preferably 0.001% by mass to 0.5% by mass.

-Other Ingredients-

Other ingredients are not particularly limited and may be selected from known ingredients accordingly and examples include diluents, waxes, macromolecular components, solvents, plasticizers, colorants, desiccant and preservatives. These may be used alone or in combination.

The other ingredients are preferably the ingredients safely absorbed in the body after oral uptake and may be the ingredients appropriately synthesized and/or prepared (extracted) or the ingredients offered commercially.

The content of the other ingredients is not particularly limited and may be adjusted accordingly within the range without impairing the effect of the present invention.

The diluents are not particularly limited and may be selected accordingly as long as they are capable of dissolving the enzymatically decomposed lecithin and examples include medium chain fatty acid triglyceride, octyldecyl triglyceride, liquid paraffin and glycerin monooleate. These may be used alone or in combination.

The waxes are defined so as to include fat which contain ester of fatty acid and glycerin as a main ingredient besides waxes which contain ester of fatty acid and higher monoalcohol and ester of fatty acid and higher dihydric alcohol as main ingredients. The waxes are not particularly limited and may be selected from known waxes for use accordingly as long as they are capable of improving anti-sticking effect of soft capsules and the wax is preferably at least one selected from natural wax and fat.

The natural wax is not particularly limited and may be selected accordingly as long as it is a wax of natural origin and examples include vegetable wax, animal wax, mineral wax and petroleum wax.

Examples of vegetable wax include candelilla wax, carnauba wax, rice bran wax, ouricury wax, sugarcane wax, jojoba wax and sunflower wax.

Examples of animal wax include yellow beeswax, lanolin and shellac wax.

Examples of mineral wax include montan wax, ozokerite and ceresin.

Examples of petroleum wax include microcrystalline wax, paraffin wax and petrolatum.

Examples of fat include beef fat, lard, cacao butter, palm oil, hardened castor oil, hardened rapeseed oil, hardened cotton-seed oil, hardened soybean oil, hard fat, japan wax and the like.

The macromolecular component is not particularly limited and may be selected from known macromolecular components accordingly as long as it is capable of improving anti-sticking effect of the soft capsules and examples include polysaccharide.

The solvent is not particularly limited and may be selected accordingly and examples include aqueous solvent. The suitable examples of aqueous solvent include water, alcohol and combined solvent of water and alcohol.

The capsule anti-sticking agent of the present invention can be used for coating surfaces of various capsules which need prevention of surface sticking and can be suitably used as so-called covering agent for soft capsules. Since the capsule anti-sticking agent of the present invention can effectively prevent sticking between the soft capsules and between the soft capsules and the containers when stored in high temperature and high humidity environment (at a temperature of 40° C. and a relative humidity of 75% or more, for example), it can be suitably used as a covering agent of soft capsules such as medicaments and foods, and the like in particular.

(Coated Soft Capsule)

The coated soft capsule of the present invention contains the capsule anti-sticking agent of the present invention applied to its surface.

The soft capsule with the surface being coated with the capsule anti-sticking agent may be selected from known soft capsules accordingly and it may be a soft capsule offered commercially or appropriately manufactured. And the soft capsule may be the one in which medicine is contained internally or the one without medicine.

The membrane material of the soft capsules is not particularly limited and may be selected accordingly. Examples include membrane materials made of gelatin, agar, carrageenan, alginic acid or salt thereof, gums (gum arabic, gellan gum, xanthan gum, and the like, for example) and celluloses (HPMC, HPC, HEC, CMEC, HPMCP, and the like, for example) which are added with appropriate plasticizers.

Examples of the plasticizer include glycerin, polyvinyl alcohol, sorbitol, mannitol, polyethylene glycols and polyvinyl pyrolidone.

Furthermore, colorant, preservative, aromatic, flavoring agents, odor improving agents and the like may be added to the membrane material as necessary.

The method for manufacturing soft capsules is not particularly limited and may be selected from known methods for manufacturing and examples include plate process method, rotary die method and seamless method.

The rotary die method is a method for manufacturing soft capsules continuously by supplying two membrane sheets for soft capsules (wall material sheet for soft capsules shell) between a pair of cylindrical molds for molding capsules which rotates in an opposing direction (JP-A Nos. 4-27352 and 8-57022).

The seamless method is a method for manufacturing soft capsules in which capsule contents in liquid form from the inner outlet of the nozzle of double or triple structure and capsule membrane material in liquid form (capsule wall material liquid) from the outer outlet of the nozzle are discharged into oily liquid or gas at a constant speed by means of pump or gravity respectively, the discharged liquid is cut at regular intervals by physical force such as oscillation, impact, flow rate difference of each liquid or gas, etc. and the cut section is made round by boundary tension or surface tension between oily liquid or gas and the capsule membrane liquid (capsule wall material liquid) (JP-A No. 7-196478).

The shape of the soft capsule is not particularly limited and may be selected accordingly. Examples include round type (ball), football type (oval), oblong type, tube type, square type, heart type and self-cut type.

The size of the soft capsule is not particularly limited and may be selected accordingly.

A surface of the coated soft capsule is coated with the capsule anti-sticking agent of the present invention and the coated soft capsule can be suitably manufactured by the method for manufacturing the coated soft capsule of the present invention which will be described later.

The coated soft capsule of the present invention can be suitably used in various fields, particularly in the fields of medicaments, cosmetics, foods and health foods. The coated soft capsule of the present invention excels in anti-sticking effect, is of high quality without impairment of various properties such as water activity, disintegration property and safety compared to the conventional soft capsules without the capsule anti-sticking agent on the surfaces. The coated soft capsule prevents sticking between capsules and to the storage containers even when stored in high temperature and high humidity environment (at a temperature of 40° C. and a relative humidity of 75% or more, for example).

(Method for Manufacturing the Coated Soft Capsule)

The method for manufacturing the coated soft capsule of the present invention is a method in which surfaces of the soft capsules are coated using the capsule anti-sticking agent of the present invention described above and further includes other steps suitably selected as necessary.

The method for applying capsule anti-sticking agent is not particularly limited and may be selected accordingly. Examples include a method in which a coating liquid of the capsule anti-sticking agent in which enzymatically decomposed lecithin is dissolved in a diluent such as medium chain fatty acid triglyceride is sprayed to the surfaces of the soft capsules (fluid bed method) and a method in which soft capsules are dipped in a coating liquid in which the capsule anti-sticking agent is dissolved.

It is possible to efficiently manufacture soft capsules of high quality which excel in anti-sticking effect only by applying the capsule anti-sticking agent of the present invention on the surfaces of the soft capsules in the method for manufacturing the coated soft capsule of the present invention.

EXAMPLES

The invention is explained in detail referring to Examples and Comparative Examples below, and the following Examples and Comparative Examples should not be construed as limiting the scope of this invention.

-Preparation of Capsule Anti-Sticking Agent-

Examples 1 to 4

The capsule anti-sticking agents (A-1 to A-4) of Examples 1 to 4 were prepared by adding and mixing an enzymatically decomposed lecithin ("SLP-White Lyso" by Tsuji Oil Mill Co., Ltd.) in a medium chain fatty acid triglyceride ("Panaset 810" by NOF Corporation) in a ratio as shown in Table 1 respectively. The enzymatically decomposed lecithin is "a purified enzymatically decomposed lecithin" obtained by purifying the enzymatic decomposition product of lecithin of soybean origin.

Examples 5 to 8

The capsule anti-sticking agents (B-1 to B-4) of Examples 5 to 8 were prepared by adding and mixing an enzymatically decomposed lecithin ("SLP-Paste Lyso" by Tsuji Oil Mill Co., Ltd.) in a medium chain fatty acid triglyceride ("Panaset 810" by NOF Corporation) in a ratio as shown in Table 1 respectively. The enzymatically decomposed lecithin is an enzymatic decomposition product of lecithin of soybean origin.

Examples 9 and 10

The capsule anti-sticking agents (C-1 and C-2) of Examples 9 and 10 were prepared by adding and mixing an enzymatically decomposed lecithin ("Egg Yolk Lysolecithin LPC-1" by Kewpie Co., Ltd.) in a medium chain fatty acid triglyceride ("Panaset 810" by NOF Corporation) in a ratio as shown in Table 1 respectively. The enzymatically decomposed lecithin is an enzymatic decomposition product of egg yolk lecithin.

Comparative Examples 1 and 2

The capsule anti-sticking agents (D-1 and D-2) of Comparative Examples 1 and 2 were prepared by adding and mixing a purified lecithin ("SLP-White" by Tsuji Oil Mill Co., Ltd.) in a medium chain fatty acid triglyceride ("Panaset 810" by NOF Corporation) in a ratio as shown in Table 1 respectively. The purified lecithin is a purified unrefined lecithin of soybean origin.

Comparative Examples 3 and 4

The capsule anti-sticking agents (E-1 and E-2) of Comparative Examples 3 and 4 were prepared by adding and mixing a hydrogenated lecithin ("SLP-White H" by Tsuji Oil Mill Co., Ltd.) in a medium chain fatty acid triglyceride ("Panaset 810" by NOF Corporation) in a ratio as shown in Table 1 respectively. The hydrogenated lecithin is a hydrogenated product of purified lecithin which is a purified unrefined lecithin of soybean origin.

Comparative Examples 5 to 7

The capsule anti-sticking agents (F-1 to F-3) of Comparative Examples 5 to 7 were prepared by adding and mixing a lecithin ("Soy Lecithin" by Tsuji Oil Mill Co., Ltd.) in a medium chain fatty acid triglyceride ("Panaset 810" by NOF Corporation) in a ratio as shown in Table 1 respectively.

Comparative Examples 8 to 12

The capsule anti-sticking agent (G) of Comparative Example 8 was prepared by adding and mixing a purified candelilla wax ("Purified Candelilla Wax Special Edition" by Cera Rica Noda Co., Ltd.) in a medium chain fatty acid triglyceride ("Panaset 810" by NOF Corporation) in a ratio as shown in Table 1. The capsule anti-sticking agent (H) of Comparative Example 9 was prepared by adding and mixing a rice wax ("Rice Wax F-1" by Cera Rica Noda Co., Ltd.) in a medium chain fatty acid triglyceride ("Panaset 810" by NOF Corporation) in a ratio as shown in Table 1. The capsule anti-sticking agent (I) of Comparative Example 10 was prepared by adding and mixing a purified lanolin (official) ("Purified Lanolin" by Nippon Fine Chemical Co., Ltd.) in a medium chain fatty acid triglyceride ("Panaset 810" by NOF Corporation) in a ratio as shown in Table 1. The capsule anti-sticking agent (J) of Comparative Example 11 was prepared by adding and mixing a paraffin wax ("Paraffin Wax-125" by Nippon Seiro Co., Ltd.) in a medium chain fatty acid triglyceride ("Panaset 810" by NOF Corporation) in a ratio as shown in Table 1. The capsule anti-sticking agent (K) of Comparative Example 12 was prepared by adding and mixing a white wax ("White Wax-M" by Araki Seiro Limited Partnership) in a medium chain fatty acid triglyceride ("Panaset 810" by NOF Corporation) in a ratio as shown in Table 1.

TABLE 1

| | | Capsule Antisticking Agent | |
|---|---|---|---|
| | No. | Active Ingredient | Content (% by mass) |
| Ex. 1 | A-1 | Purified Enzymatically Decomposed Lecithin | 0.05 |
| Ex. 2 | A-2 | Purified Enzymatically Decomposed Lecithin | 0.125 |
| Ex. 3 | A-3 | Purified Enzymatically Decomposed Lecithin | 0.25 |
| Ex. 4 | A-4 | Purified Enzymatically Decomposed Lecithin | 0.02 |
| Ex. 5 | B-1 | Enzymatically Decomposed Lecithin | 0.1 |
| Ex. 6 | B-2 | Enzymatically Decomposed Lecithin | 0.25 |
| Ex. 7 | B-3 | Enzymatically Decomposed Lecithin | 0.5 |
| Ex. 8 | B-4 | Enzymatically Decomposed Lecithin | 1.0 |
| Ex. 9 | C-1 | Enzymatically Decomposed Lecithin | 0.02 |
| Ex. 10 | C-2 | Enzymatically Decomposed Lecithin | 0.05 |
| Comp. Ex. 1 | D-1 | Purified Lecithin | 1.0 |
| Comp. Ex. 2 | D-2 | Purified Lecithin | 2.0 |
| Comp. Ex. 3 | E-1 | Hydrogenated Lecithin | 0.25 |
| Comp. Ex. 4 | E-2 | Hydrogenated Lecithin | 0.5 |
| Comp. Ex. 5 | F-1 | Lecithin | 3.0 |
| Comp. Ex. 6 | F-2 | Lecithin | 6.0 |
| Comp. Ex. 7 | F-3 | Lecithin | 9.0 |
| Comp. Ex. 8 | G | Purified Candelilla Wax | 0.01 |
| Comp. Ex. 9 | H | Rice Wax | 0.01 |
| Comp. Ex. 10 | I | Purified Lanolin (official) | 0.01 |
| Comp. Ex. 11 | J | Paraffin Wax | 0.01 |
| Comp. Ex. 12 | K | White Wax | 0.01 |

-Manufacture and Evaluation of Coated Soft Capsules-

Examples 11 to 17 and Comparative Examples 13 to 24

(1) Manufacture of Soft Capsules

By using the membrane material composition for soft capsules as shown in the following Table 2, 5,000 capsules of the oval 3 type soft capsules containing 100 mg of d-alpha-tocopherol acetate per one capsule were manufactured by rotary die method.

TABLE 2

| Membrane Material Composition for Soft Capsules | | |
|---|---|---|
| Raw Material | Mass Ratio | Feed Amount (kg) |
| Gelatin | 100.0 | 140.0 |
| Concentrated Glycerin | 20.0 | 28.0 |
| D-Sorbitol Solution | 10.0 | 14.0 |
| Ethyl p-hydroxybenzoate | 0.3 | 0.42 |
| Propyl p-hydroxybenzoate | 0.1 | 0.14 |
| L-Asparagic Acid | 2.0 | 2.8 |
| Purified Water | Moderate Amount | 132.5 |

(2) Manufacture of Coated Soft Capsules

The coated soft capsules of Examples 11 to 17 and Comparative Examples 13 to 24 were manufactured by applying the capsule anti-sticking agents of Examples 1 to 3 and 5 to 8 and Comparative Examples 1 to 12 shown in Table 1 to the soft capsules manufactured as above and drying by fluid bed method.

(3) Evaluation

The adhesive property, disintegration property and water activity were evaluated for each obtained coated soft capsule according to the methods described in the following.

<Evaluation of Adhesive Property>

The evaluation of adhesive property was performed by the following adhesive property tests 1 to 3.

<<Adhesive Property Test 1>>

Each of the 50 soft capsules that were manufactured by the methods of Examples 11 to 17 or Comparative Examples 13 to 24 was put in storage containers made of the polyester resin. And the containers were stored in a constant temperature and moisture chamber at a temperature of 25° C. and a relative humidity of 75% or a constant temperature and moisture chamber at a temperature of 40° C. and a relative humidity of 75% for 2 weeks or 4 weeks respectively, and then were taken out.

The storage containers which had been taken out were gently inverted, and then the conditions of the coated soft capsules in the storage containers were observed with eyes. As a result, the coated soft capsules were either sticking to the inner surface of the storage containers or sticking to each other.

Next, the storage containers were dropped freely on the concrete floor surface and a number of times till all the coated soft capsules sticking in the storage containers were separated was measured and evaluated according to the Evaluation Criteria below.

As a dropping condition of the storage containers, the maximum number of dropping times from a height of approximately 1 cm from the floor surface was set at 3, and when sticking of the coated soft capsules were still observed after 3 times of dropping, the storage containers were then dropped from a height of approximately 5 cm from the floor surface. The maximum number of dropping times from the height of approximately 5 cm from the floor surface was set at 10 and when sticking of the coated soft capsules were still observed after 10 times of dropping, the storage containers were then dropped from a height of approximately 10 cm from the floor surface. The results of dropped height and number of times are shown in Table 3.

From the results shown in Table 3, it turns out that the coated soft capsules of Examples 11 to 17 which are coated with the capsule anti-sticking agent of the present invention of Examples 1 to 3 and 5 to 8 have low adhesive properties between the coated soft capsules and to the containers even after being stored in a condition at 25° C. and 75% relative humidity and a condition at 40° C. and 75% relative humidity for 4 weeks.

<<Adhesive Property Test 2>>

Each of the 2,000 soft capsules that were manufactured by the methods of Examples 11 to 17 or Comparative Examples 13 to 24 was put in polyethylene bags respectively and further put in a metal can of 18 L volume. And the metal cans were stored in a constant temperature and moisture chamber at a temperature of 23° C. and a relative humidity of 50% for 2 weeks.

The metal can were taken out from the constant temperature and moisture chamber, and then the sticking conditions of the coated soft capsules right after the polyethylene bags were taken out and when the polyethylene bags were placed on the floor were observed with eyes and evaluated by the Evaluation Criteria below. The results are shown in Table 4.

[Evaluation Criteria]

A: a small number of capsules had adhered, but quickly separated with their own weight B: capsules had adhered at the bottom surface portion in some degree but separated with their own weight C: capsules had adhered, and did not separate completely even when pressed by hand D: capsules had adhered entirely, and only about half of the capsules were separated when pressed by hand Meanwhile, capsules evaluated as "A" and "B" in the above evaluation have no problem for practical use. The capsules evaluated as "C" are needed to be separated when used and are not practical for use because of bad workability. The capsules evaluated as "D" have extremely bad workability when used and are not practical for use.

TABLE 3

| | Capsule Antisticking Agent | Storing Condition (25° C., 75 RH %) | | | | | Storing Condition (40° C., 75 RH %) | | | | |
|---|---|---|---|---|---|---|---|---|---|---|---|
| | | After 2 Weeks | | After 4 Weeks | | | After 2 Weeks | | After 4 Weeks | | |
| | | 1 cm | 5 cm | 1 cm | 5 cm | 10 cm | 1 cm | 5 cm | 1 cm | 5 cm | 10 cm |
| Ex. 11 | A-1 | 1 | 0 | 2 | 0 | 0 | 3 | 3 | 3 | 2 | 0 |
| Ex. 12 | A-2 | 1 | 0 | 2 | 0 | 0 | 3 | 3 | 3 | 1 | 0 |
| Ex. 13 | A-3 | 1 | 0 | 1 | 0 | 0 | 3 | 3 | 3 | 2 | 0 |
| Ex. 14 | B-1 | 1 | 0 | 1 | 0 | 0 | 3 | 2 | 3 | 2 | 0 |
| Ex. 15 | B-2 | 1 | 0 | 1 | 0 | 0 | 3 | 1 | 3 | 1 | 0 |
| Ex. 16 | B-3 | 1 | 0 | 1 | 0 | 0 | 3 | 1 | 3 | 1 | 0 |
| Ex. 17 | B-4 | 1 | 0 | 2 | 0 | 0 | 3 | 2 | 3 | 1 | 0 |
| Comp. Ex. 13 | D-1 | 1 | 0 | 2 | 0 | 0 | 3 | 1 | 3 | 1 | 0 |
| Comp. Ex. 14 | D-2 | 1 | 0 | 1 | 0 | 0 | 3 | 1 | 3 | 1 | 0 |
| Comp. Ex. 15 | E-1 | 1 | 0 | 1 | 0 | 0 | 3 | 2 | 3 | 1 | 0 |
| Comp. Ex. 16 | E-2 | 1 | 0 | 2 | 0 | 0 | 3 | 2 | 3 | 2 | 0 |
| Comp. Ex. 17 | F-1 | 2 | 0 | 1 | 0 | 0 | 3 | 1 | 3 | 2 | 0 |
| Comp. Ex. 18 | F-2 | 1 | 0 | 2 | 0 | 0 | 3 | 2 | 3 | 1 | 0 |
| Comp. Ex. 19 | F-3 | 1 | 0 | 1 | 0 | 0 | 3 | 1 | 3 | 1 | 0 |
| Comp. Ex. 20 | G | 1 | 0 | 3 | 10 | 3 | 1 | 0 | 3 | 10 | 3 |
| Comp. Ex. 21 | H | 1 | 0 | 3 | 10 | 10< | 1 | 0 | 3 | 10 | 10< |
| Comp. Ex. 22 | I | 1 | 0 | 3 | 10 | 10< | 1 | 0 | 3 | 10 | 10< |
| Comp. Ex. 23 | J | 1 | 0 | 3 | 10 | 10< | 1 | 0 | 3 | 10 | 10< |
| Comp. Ex. 24 | K | 1 | 0 | 3 | 10 | 10< | 1 | 0 | 3 | 10 | 10< |

TABLE 4

| | Antisticking Agent | Evaluation |
|---|---|---|
| Ex. 11 | A-1 | A |
| Ex. 12 | A-2 | A |
| Ex. 13 | A-3 | A |
| Ex. 14 | B-1 | A |
| Ex. 15 | B-2 | B |
| Ex. 16 | B-3 | B |
| Ex. 17 | B-4 | B |
| Comp. Ex. 13 | D-1 | C |
| Comp. Ex. 14 | D-2 | C |
| Comp. Ex. 15 | E-1 | C |
| Comp. Ex. 16 | E-2 | C |
| Comp. Ex. 17 | F-1 | D |
| Comp. Ex. 18 | F-2 | D |
| Comp. Ex. 19 | F-3 | D |

From the results shown in Table 4, it turns out that the coated soft capsules of Examples 11 to 17 excel in anti-sticking effect compared to the coated soft capsules of Comparative Examples 13 to 19 after storing in a condition of 23° C. temperature and 50% relative humidity for 2 weeks.

<<Adhesive Property Test 3>>

After evaluation of the adhesive property test 2, the coated soft capsules that were manufactured by the methods of Examples 11 to 17 or Comparative Examples 13, 15 and 16 were again put in a metal can while capsules of each Example were still packed in polyethylene bags. And the metal cans were stored in a constant temperature and moisture chamber at a temperature of 23° C. and a relative humidity of 50% for 5 months.

The metal cans were taken out from the constant temperature and moisture chamber, and then the sticking conditions of the coated soft capsules right after the polyethylene bags were taken out and when the polyethylene bags were placed on the floor were observed with eyes and evaluated by the same Evaluation Criteria as for the adhesive test 2. The results are shown in Table 5.

TABLE 5

| | Antisticking Agent | Evaluation |
|---|---|---|
| Ex. 11 | A-1 | A |
| Ex. 12 | A-2 | B |
| Ex. 13 | A-3 | A |
| Ex. 14 | B-1 | B |
| Ex. 15 | B-2 | B |
| Ex. 16 | B-3 | A |
| Ex. 17 | B-4 | A |
| Comp. Ex. 13 | D-1 | C |
| Comp. Ex. 15 | E-1 | C |
| Comp. Ex. 16 | E-2 | C |

From the results shown in Table 5, it turns out that the coated soft capsules of Examples 11 to 27 excel in anti-sticking effect compared to the coated soft capsules of Comparative Examples 13, 15 and 16 even after further storage in a condition of 23° C. temperature and 50% relative humidity for 5 months.

From the results shown in Tables 3 to 5, it turns out that approximately the same results were obtained for the coated soft capsules of Comparative Examples 13 to 19 as for the coated soft capsules of Examples 11 to 17 in the adhesive property test 1. However, the coated soft capsules of Comparative Examples 13 to 19 were clearly inferior to the coated soft capsules of Examples 11 to 17 in terms of anti-sticking effect in the adhesive property tests 2 and 3 which imitate the storage condition of the manufacturing site.

Judging from the results of the adhesive property tests 1 to 3 comprehensively on a basis of the above results, it turns out that the coated soft capsules of Examples 11 to 17 have no problem for practical use, and on the other hand, the coated soft capsules of Comparative Examples 13 to 24 are not practical for use.

<Disintegration Test>

From the storage containers taken out from the constant temperature and moisture chamber in the adhesive property test 1, 6 capsules were taken out randomly for each coated soft capsules and put in a bucket so that each tube was filled with one capsule. The bucket was then put in a beaker filled with purified water heated at 37° C. and left unattended for 15 minutes. After then, the bucket was taken out from the beaker, the dissolving conditions of the coated soft capsules were observed with eyes and the number of the coated soft capsules which did not dissolve completely (residual number of capsules) were measured. The results are shown in Table 6.

TABLE 6

| | Antisticking Agent | Storing Condition (25° C., 75 RH %) | | Storing Condition (40° C., 75 RH %) | |
|---|---|---|---|---|---|
| | | After 2 Weeks | After 4 Weeks | After 2 Weeks | After 4 Weeks |
| Ex. 11 | A-1 | 0 | 0 | 0 | 0 |
| Ex. 12 | A-2 | 0 | 0 | 0 | 0 |
| Ex. 13 | A-3 | 0 | 0 | 0 | 0 |
| Ex. 14 | B-1 | 0 | 0 | 0 | 0 |
| Ex. 15 | B-2 | 0 | 0 | 0 | 0 |
| Ex. 16 | B-3 | 0 | 0 | 0 | 0 |
| Ex. 17 | B-4 | 0 | 0 | 0 | 0 |
| Comp. Ex. 13 | D-1 | 0 | 0 | 0 | 1 |
| Comp. Ex. 14 | D-2 | 0 | 0 | 0 | 0 |
| Comp. Ex. 15 | E-1 | 0 | 0 | 0 | 1 |
| Comp. Ex. 16 | E-2 | 0 | 0 | 0 | 1 |
| Comp. Ex. 17 | F-1 | 0 | 1 | 0 | 0 |
| Comp. Ex. 18 | F-2 | 0 | 1 | 0 | 0 |
| Comp. Ex. 19 | F-3 | 0 | 0 | 0 | 0 |

From the results shown in Table 6, it turns out that the residual number of capsules of the coated soft capsules of Examples 11 to 17 was equal to or fewer than those of the coated soft capsules of Comparative Examples 13 to 19 and disintegration property was not affected with the application of the anti-sticking agent of the present invention.

<Measurement of Water Activity Value>

From the storage containers taken out from the constant temperature and moisture chamber in the adhesive property test 1, 10 capsules were taken out randomly for each coated soft capsules, put in a measurement container of an water activity measuring equipment (by Novasina) and the water activity values were measured after leaving the container unattended for 15 minutes to 20 minutes to stabilize the water activity measurement curve. The results are shown in Table 7.

TABLE 7

| | Antisticking Agent | Storing Condition (25° C., 75 RH %) | | Storing Condition (40° C., 75 RH %) | |
|---|---|---|---|---|---|
| | | After 2 Weeks | After 4 Weeks | After 2 Weeks | After 4 Weeks |
| Comparative Product | none | 0.454 | 0.444 | 0.446 | 0.447 |
| Ex. 11 | A-1 | 0.437 | 0.438 | 0.437 | 0.437 |
| Ex. 12 | A-2 | 0.427 | 0.431 | 0.428 | 0.428 |
| Ex. 13 | A-3 | 0.446 | 0.449 | 0.449 | 0.448 |
| Ex. 14 | B-1 | 0.448 | 0.450 | 0.436 | 0.442 |
| Ex. 15 | B-2 | 0.389 | 0.442 | 0.446 | 0.440 |

TABLE 7-continued

| | Antisticking Agent | Storing Condition (25° C., 75 RH %) | | Storing Condition (40° C., 75 RH %) | |
|---|---|---|---|---|---|
| | | After 2 Weeks | After 4 Weeks | After 2 Weeks | After 4 Weeks |
| Ex. 16 | B-3 | 0.449 | 0.450 | 0.435 | 0.448 |
| Ex. 17 | B-4 | 0.432 | 0.432 | 0.441 | 0.432 |
| Comp. Ex. 13 | D-1 | 0.440 | 0.448 | 0.450 | 0.456 |
| Comp. Ex. 14 | D-2 | 0.423 | 0.429 | 0.429 | 0.433 |
| Comp. Ex. 15 | E-1 | 0.429 | 0.430 | 0.432 | 0.436 |
| Comp. Ex. 16 | E-2 | 0.418 | 0.420 | 0.423 | 0.424 |
| Comp. Ex. 17 | F-1 | 0.452 | 0.457 | 0.451 | 0.456 |
| Comp. Ex. 18 | F-2 | 0.431 | 0.431 | 0.429 | 0.426 |
| Comp. Ex. 19 | F-3 | 0.438 | 0.396 | 0.437 | 0.433 |

From the results shown in Table 7, the coated soft capsules of Examples 11 to 17 and Comparative Examples 13 to 19 exhibited approximately equivalent water activity value relative to the comparative product which was not coated with a capsule anti-sticking agent and it turns out that the application of the capsule anti-sticking agent brings no adverse effect on the water activity values.

Examples 18 to 20

(1) Manufacture of Soft Capsules

By using the membrane material compositions of the soft capsules shown in Table 2, 5,000 oval 3 type soft capsules were manufactured as similar to Example 11.

(2) Manufacture of Coated Soft Capsules

The coated soft capsules of Examples 18 to 20 were manufactured by applying the capsule anti-sticking agents of Examples 4, 9 and 10 shown in Table 1 to the soft capsules manufactured as above and drying by fluid bed method.

(3) Evaluation

Each of the 50 soft capsules was put in storage containers made of the polyester resin. And the containers were stored in a constant temperature and moisture chamber at a temperature of 25° C. and a relative humidity of 75% or a constant temperature and moisture chamber at a temperature of 40° C. and a relative humidity of 75% for 4 weeks, and then were taken out.

The storage containers which had been taken out were gently inverted, and then the conditions of the coated soft capsules in the storage containers were observed with eyes. As a result, the coated soft capsules were either sticking to the inner surface of the storage containers or sticking to each other.

Next, the storage containers were dropped freely on the concrete floor surface and a number of times till all the coated soft capsules sticking in the storage containers were separated was measured and evaluated according to the evaluation standards below.

As a dropping condition of the storage containers, the maximum number of dropping times from a height of approximately 1 cm from the floor surface was set at 3, and when sticking of the coated soft capsules were still observed after 3 times of dropping, the storage containers were then dropped from a height of approximately 5 cm from the floor surface. The maximum number of dropping times from the height of approximately 5 cm from the floor surface was set at 10 and when sticking of the coated soft capsules were still observed after 10 times of dropping, the storage containers were then dropped from a height of approximately 10 cm from the floor surface. The results of dropped height and number of times are shown in Table 8.

TABLE 8

| | Antisticking Agent | Storing Condition (25° C., 75 RH %) | | | Storing Condition (40° C., 75 RH %) | | |
|---|---|---|---|---|---|---|---|
| | | 1 cm | 5 cm | 10 cm | 1 cm | 5 cm | 10 cm |
| Ex. 18 | A-4 | 3 | 0 | 0 | 3 | 10 | 1 |
| Ex. 19 | C-1 | 2 | 0 | 0 | 3 | 9 | 0 |
| Ex. 20 | C-2 | 1 | 0 | 0 | 3 | 10 | 1 |

From the results shown in Table 8, it turns out that the coated soft capsules of Example 18 which were coated with the capsule anti-sticking agent containing an enzymatically decomposed lecithin of soy bean origin of Example 4, and the coated soft capsules of Examples 19 to 20 which were coated with the enzymatically decomposed lecithin of egg yolk origin of Examples 9 to 10 show equivalent anti-sticking effects.

By the present invention, it is possible to solve existing problems and to provide a capsule anti-sticking agent which can provide excellent anti-sticking effect on a soft capsule without impairing various properties such as water activity, disintegration property and safety, a coated soft capsule of high quality which is coated with the capsule anti-sticking agent and excels in anti-sticking effect, and an efficient method for manufacturing the coated soft capsule. Since the coated soft capsule of the present invention can effectively prevent sticking between the coated soft capsules and to the containers of the coated soft capsules, it is suitably used in various fields, particularly in the fields of medicaments, foods, cosmetics and health foods.

What is claimed is:

1. A coated soft capsule, comprising: a capsule anti-sticking agent, wherein a surface of the coated soft capsule is coated with the capsule anti-sticking agent, and the capsule anti-sticking agent comprises an enzymatically decomposed lecithin,
wherein the enzymatically decomposed lecithin includes one or more selected from lysolecithin, phosphatidyl acid, and phosphatidyl glycerol, and
wherein content of the enzymatically decomposed lecithin relative to whole amount of the capsule anti-sticking agent is 0.0001% by mass to 2.0% by mass.

2. A method for manufacturing a coated soft capsule, comprising: applying a capsule anti-sticking agent on a surface of a soft capsule, wherein the capsule anti-sticking agent comprises an enzymatically decomposed lecithin,
wherein the enzymatically decomposed lecithin includes one or more selected from lysolecithin, phosphatidyl acid, and phosphatidyl glycerol, and
wherein content of the enzymatically decomposed lecithin relative to whole amount of the capsule anti-sticking agent is 0.0001% by mass to 2.0% by mass.

* * * * *